United States Patent [19]

Coulter et al.

[11] 3,944,797
[45] Mar. 16, 1976

[54] METHOD AND APPARATUS FOR DETERMINING THE CORRECT PERCENTILES OF THE SIZE DISTRIBUTION OF A PARTICULATE SYSTEM

[75] Inventors: Wallace H. Coulter, Miami Springs; Walter R. Hogg, Miami Lakes, both of Fla.

[73] Assignee: Coulter Electronics, Inc., Hialeah, Fla.

[22] Filed: Aug. 6, 1974

[21] Appl. No.: 495,230

[52] U.S. Cl. ...... 235/151.3; 324/71 CP; 235/92 PC
[51] Int. Cl.² ..................... G01N 15/02; G06G 7/12
[58] Field of Search ........ 235/151.3, 92 PC, 151.35, 235/185, 193.5; 324/71

[56] References Cited
UNITED STATES PATENTS

| | | | |
|---|---|---|---|
| 3,557,352 | 1/1971 | Hogg et al. | 235/151.3 |
| 3,812,335 | 5/1974 | Coulter et al. | 235/151.3 |

Primary Examiner—Edward J. Wise
Attorney, Agent, or Firm—Silverman & Cass

[57] ABSTRACT

An apparatus for determining the correct particle sizes at predetermined percentiles of the size distribution of a particulate system having a known size distribution characteristic such as for example a normal or log-normal size distribution, wherein a portion of the particles are too small to be measured. The particulate system is first passed through a particle detecting device which can be of the Coulter type. The particle detecting device produces particle pulses proportional to the size of the particles in the particulate system which can be measured. At least three percentile size determining circuits receive the particle pulses and develop first, second and third particle size signals respectively, indicating the size of the particles in the particulate system at the first, second and third predetermined percentiles. Two of the size signals are combined in a particular manner based on the known size distribution characteristic for the type of particulate system to yield a combined signal which approximates or is and estimate of the third percentile signal. The combined signal is compared with the measured third signal to obtain an error signal. The error signal is used in turn to add into all three size percentile circuits compensation or correction signals for the total volume of particles too small to be included in the measurements. This process causes the error signal to decrease toward zero, and results in all three circuits having outputs truly representative of their nominal percentiles.

26 Claims, 5 Drawing Figures

METHOD AND APPARATUS FOR DETERMINING THE CORRECT PERCENTILES OF THE SIZE DISTRIBUTION OF A PARTICULATE SYSTEM

CROSS REFERENCE TO RELATED PATENTS

This application is related to U.S. Pat. No. 3,557,352 which, to the extent necessary, is to be considered incorporated herein by this reference.

BACKGROUND OF THE INVENTION

The invention herein relates generally to the art of studying the physical properties of particulate systems and more particularly is concerned with ascertaining accurately the size distribution of particles in a particulate system.

Now well known in the art are apparatuses for measuring a dividing particle size in a particulate system. One such apparatus is shown and described in the above-noted U.S. Pat. No. 3,557,352, hereinafter terms the Mass Median apparatus and Mass Median patent, and can be used to ascertain any particular dividing particle size in a particulate system. The Mass Median apparatus employs a Coulter type particle detector such as shown and described in U.S. Pat. No. 2,656,508. Size in this and the Mass Median patent being synonymous with volume and mass because the particle pulse developed have an amplitude which is proportional to the total solid matter of the sensed particle. Since the material in the particulate system is generally known, its density is known and therefore it is easy to obtain volume by a simple mathematical conversion. Heretofore, the Mass Median apparatus was most often used to ascertain the mass median size of a particulate system which is the 50th mass percentile size. This primary usage is, of course, the basis for the apparatus name. A number of other mass percentile sizes, such as for example the 25th and 75th mass percentile sizes, can be and are determined by the Mass Median apparatus. This information provides a quickly and easily understood description of the nature of the particle distribution. Furthermore, with the information regarding the various mass percentile sizes, a size distribution curve of the particles in the particulate system can be drawn. Such curves are considered extremely useful and important in analyses of particulate systems, and in monitoring of particulate systems where a predetermined particle size distribution is to be maintained. A Mass Median apparatus such as noted above operates under the principle that it is able to measure all particle sizes. Fortunately, in many systems few particles are present which are smaller in size than can be detected by the Coulter type particle detector. In many cases, particles small enough to be undetectable constitute less than 1% of the total particulate system. In using the Mass Median apparatus for analyses of such particulate systems, errors in mass percentile sizes introduced as a result of undetected particles will be minimal.

In many particulate systems however particules are present which are smaller in size than can be detected by a Coulter type particle detector. Representative of such systems are industrial slurries wherein particles vary in size over a great range and include a large percentage of particles which are too small to be detected by a Coulter type particle detector. For purposes of this discussion, 10% is considered to constitute a large percentage of undetectably small particles in a particulate system.

If a particulate system containing for example a total of 10% undetectable particles were passed through a Mass Median apparatus, the sizes indicated by the apparatus for certain mass percentiles would be incorrect and could not be used to derive an accurate distribution curve of the particulate system. Furthermore, the sizes would be of no value in the analysis of the particulate system or in monitoring the particulate system for maintaining a correct particle distribution. Analyzing, monitoring, and maintaining such systems could only be performed after a manual classification and analysis of the particulate system, a tedious, inaccurate and expensive process.

SUMMARY OF THE INVENTION

In practicing this invention an apparatus is provided for determining the correct particle sizes at particular percentiles of the size distribution of a particulate system. The particulate system is first passed through a particle detecting device which produces particle pulses that are proportional to the total solid matter, volume or size of the particles. These pulses are coupled to first, second and third percentile size determining circuits in the apparatus. The percentile size determining circuits are operated in response to the particle pulses to develop first, second and third particle size signals respectively, indicating the size of the particles in the particulate system at the first, second and third percentiles of the size distribution of the particulate system. The first, second and third particle size signals for the first, second and third percentiles have a predetermined relationship with respect to one another. These first, second and third particle size signals are coupled to a comparison device which compares the signals in order to ascertain whether the predetermined relationship exists. The comparison device develops a comparison signal having a level which is determined by the variation of the first, second and third particle size signals from the desired predetermined relationships. This comparison signal is coupled to the first, second and third percentile size determining circuits for varying the first, second and third particle size signals so as to make them conform to the predetermined relationship with respect to one another.

A method of determining the correct particle sizes for predetermined percentiles of the size distribution of a particulate system is also envisioned as being within the scope of this invention and includes the steps of (a) developing first, second and third particle size signals in response to the above noted particle pulses indicating the size of the particles in the particulate system at first, second and third percentiles of the size distribution of a particulate system; (b) comparing the first, second and third particle size signals to ascertain the existence of a predetermined relationship with respect to one another; (c) developing a comparison signal whose level is determined by the variation of the first, second and third particle size signals from the predetermined relationship with respect to one another; (d) varying the first, second and third particle size signals in accordance with the comparison signal until the predetermined relationship of the first, second and third particle size signals with respect to one another is achieved.

DESCRIPTION OF THE PREFERRED EMBODIMENT

Figure 1:
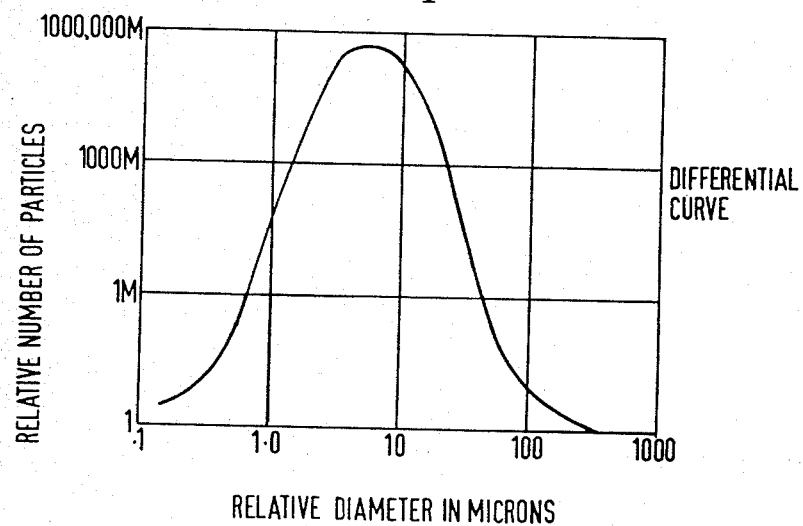
FIG. 1 is a graph illustrating the differential curve of a particulate system of relatively wide dynamic range in the classical bell shaped configuration. The logarithmic horizontal scale shows that the distribution is in log-normal form.

Referring first to FIG. 1 there is shown a bell shaped simple size distribution curve which is known as a differential curve. This curve represents the particle distribution in a particulate system. The vertical scale gives the relative number of particles in a small range and the horizontal scale gives the equivalent spherical diameter of the particles in microns. For a more complete definition of equivalent spherical diameter, reference is made to the Mass Median patent. In many industrial slurries or powders, there are so many particles that the logarithmic vertical scale is employed. In many types of particulate systems the particle distribution is known to be symmetrical about a particular size. Referencing this to FIG. 1, this means that the differential curve shown will be symmetrical about some point. A system having what is commonly termed a normal or log-normal distribution will be represented by a symmetrical differential curve. The differential curve of a normal system will be symmetrical on a graph having a linear horizontal scale, and a differential curve of a log-normal system will be symmetrical on a graph having a logarithmic horizontal scale.

Figure 2:
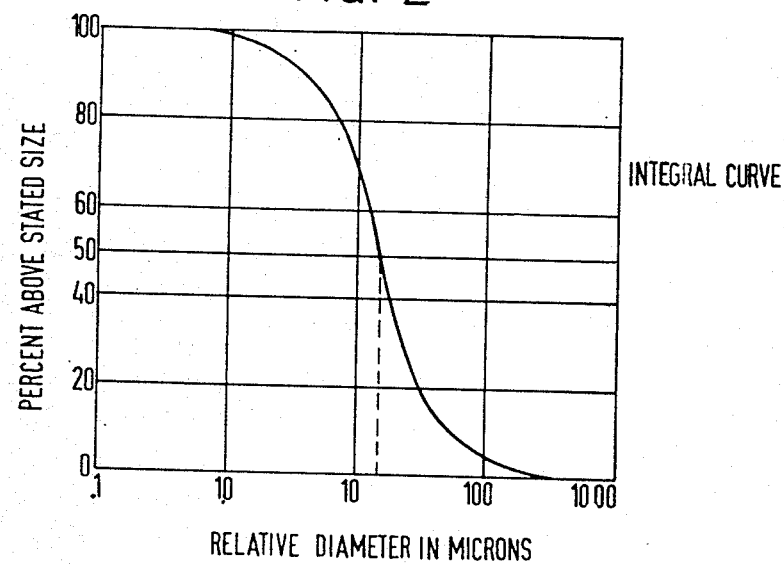
FIG. 2 is a graph illustrating the integral curve of a particulate system of relatively wide dynamic range in the classical ogive configuration.

Referring now to FIG. 2, there is shown an ogive shaped curve which is known as an integral curve of a particulate system. Since the graphs shown in FIGS. 1 and 2 are merely illustrative, it should not be assumed that they are representative of the same system. Each type can be converted to the other. Normally, a worker starts with a differential curve and converts it into an integral curve. An example of how an integral curve was prepared using classical statistical tools is given in the Mass Median patent. In FIG. 2 the vertical scale gives the percent, volume, or mass above the stated size, and the horizontal scale gives the equivalent spherical diameter of the particles in microns. The vertical scale is linear. The horizontal scale is linear if a normal system is shown and is logarithmic if a log-normal system is shown. Again, as with the differential curve, the integral curve will be symmetrical about a certain point, specifically, the 50% point on the vertical scale.

Figure 3:
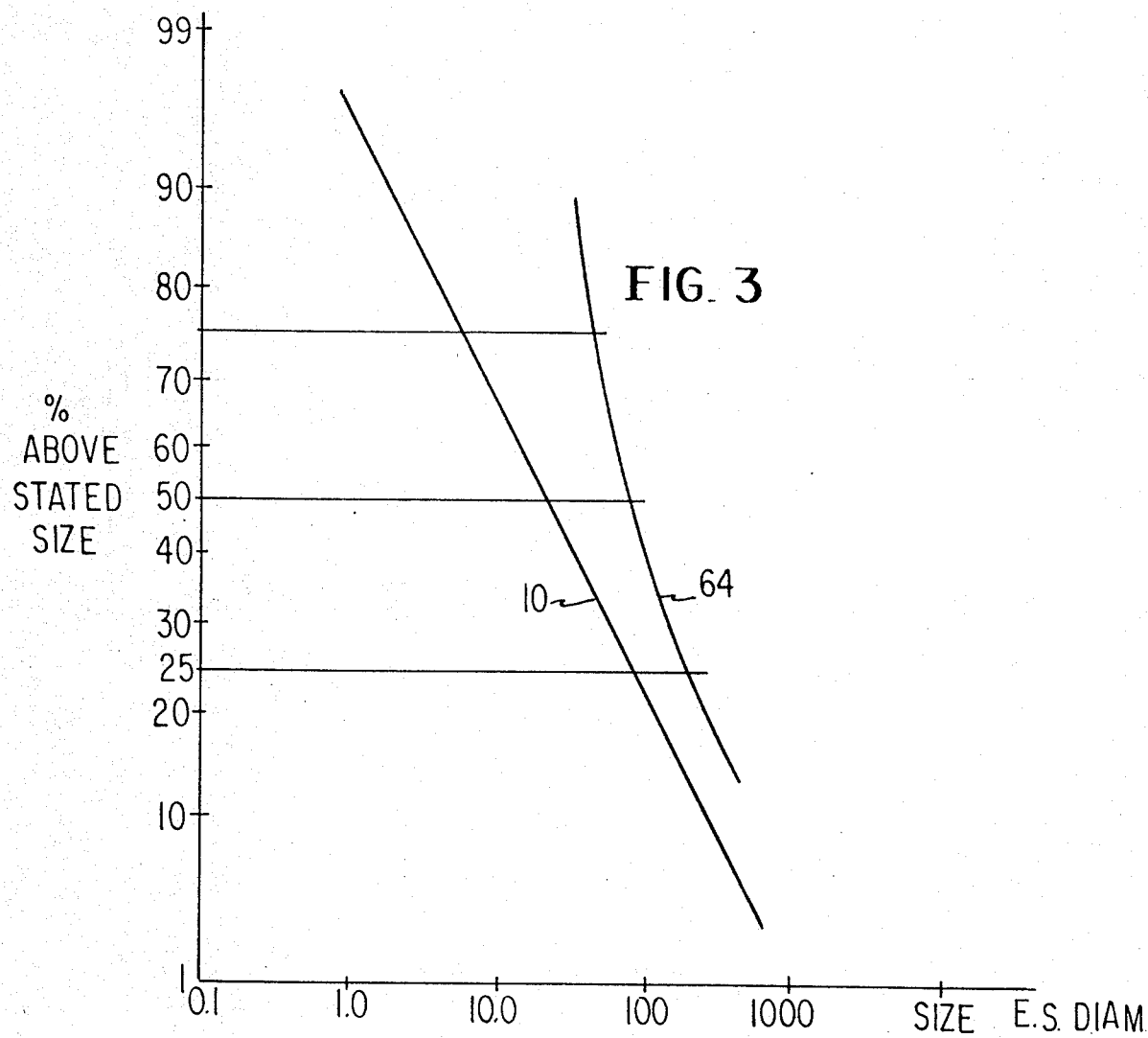
FIG. 3 is a graph illustrating the integral curve of FIG. 2 transformed onto a log probability scale and also showing a curve resulting from the operation of the apparatus of this invention.

Referring now to FIG. 3, there is shown at 10 an integral curve similar to that shown in FIG. 2 transformed onto a log-probability graph. In the log-probability graph, the vertical scale is a probability scale. On such a scale any two numbers on each side of 50% and equally numerically spaced from the 50% point will also be equally physically spaced from the 50% point. However, the upper and lower ends of the scale are stretched so that the distance between the lowest and highest numbers and the 50% point will not be proportional to the distance between intermediate numbers above and below 50%, and the 50% point. On a probability scale the vertical axis approaches minus infinity at the horizontal axis and plus infinity at the upper end of the vertical axis. The horizontal scale can be either linear or logarithmic depending on whether a normal or log-normal system is being represented. When an integral curve such as shown in FIG. 2 is redrawn on a log-probability graph, the result will be a straight line. The advantage of a straight line on a graph such as FIG. 3 is that it can be more easily extrapolated at upper size, and particularly lower size end so that a statistical analysis can be made of the size and distribution of undetectable particles. Such information can be extremely valuable in the analysis of particulate systems and in monitoring particulate systems where a predetermined particulate distribution is to be maintained.

Recognizing the symmetry of particle distribution in certain types of particulate systems, if a known normal, or log-normal system is passed through three Mass Median apparatus and the 25th, 50th and 75th mass percentile particle sizes are determined, the 25th and 75th mass percentile sizes as measured would be equally spaced in size from the 50th mass percentile size. The 25th and 75th sizes also would be symmetrical with respect to the 50th mass percentile size. If the sizes were plotted on a probability or log-probability graph, as the case may be, a straight line could be drawn between the three locations representing the numbers of particles above the three sizes. If the sizes measured do not meet one of the criteria of spacing symmetry or linear alignment, either the particulate system is not normal or log-normal, or the sizes determined would be incorrect.

As previously noted, it is generally known that many types of slurries or powders have a normal or log-normal particle distribution. If such a known particulate system were passed through three Mass Median apparatuses, and the 25th, 50th and 75th mass percentile sizes were determined, and they did not meet at least one of the above noted three criteria, the sizes determined would have to be incorrect. This, in fact, will be the case in particulate systems where any large percentage of the particles are too small to be detected by a Coulter type particle detector, or, so small that pulses developed by small particles cannot be distinguished from the noise generated by the apparatus. Because these small particles are not detected, the size determined by the Mass Median apparatuses for the 25th, 50th and 75th mass percentile sizes will be greater than is actually the case. Furthermore, because of the method of operation of the Mass Median apparatuses the failure to account for the smallest particles will affect the values for each of the 25th, 50th and 75th percentile sizes differently so that they will not meet the above noted criteria.

The method and apparatus of this invention recognizes the above noted relationships and compares the sizes determined by the Mass Median apparatuses to see if the above noted criteria is met. If it is not met, an error signal is generated which when amplified is substituted for total volume of the particles too small to be measured by combining the error signal with the signals representing the size determined by the apparatuses so that the criteria applies thus yielding mass percentile sizes corrected for inaccuracies due to nondetection of small particles.

Figure 4:
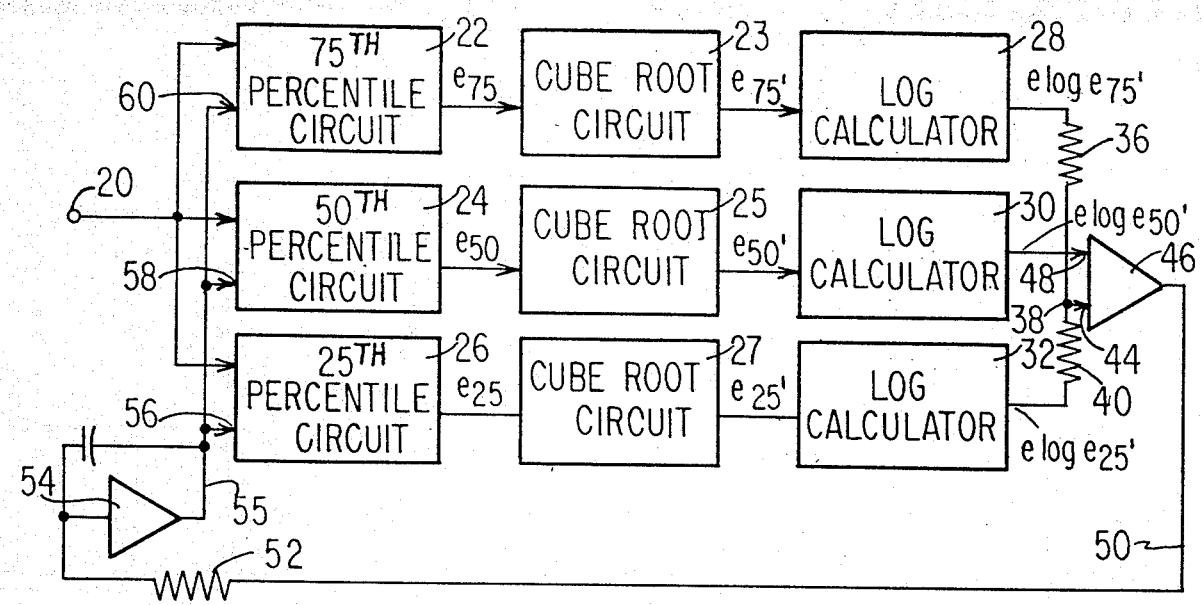
FIG. 4 is a block diagram of the apparatus of this invention.

Referring now to FIG. 4, the input terminal receives pulses from some form of particle analyzing device (not shown) which produces electrical pulses whose amplitudes are respectively proportional to the volume, mass or size of the particles producing the same. For example, such a particle analyzing device could be the electronic apparatus which operates in accordance with the Coulter principle described in U.S. Pat. No. 2,656,508. For purposes of this description it is to be assumed that the electrical pulses are produced by a Coulter type detector in response to passage of particles in a particulate system which has a log-normal distribution, and in which approximately 10% of the total particulate material is smaller than can be detected by the Coulter type particle detector.

The incoming pulses received at input terminal 20 are applied to three percentile discriminating circuits 22, 24 and 26. All three of the percentile circuits 22, 24 and 26 are of a type such as disclosed in the above noted Mass Median patent. The circuit 22 has an output voltage $e_{75}$ which is proportional to the 75th size percentile. In other words, three quarters of all particles detected have a smaller volume or size and one quarter of all particles detected have a larger volume or size than the particle size represented by the output voltage $e_{75}$. In the same manner, output voltages $e_{50}$ and $e_{25}$ represent the 50th and 25th percentile sizes. The 50the percentile size, of course, represents the mass median which in a symmetrical distribution such as a normal or log-normal distribution curve represents the peak of the differential curve and the symmetrical center of the integral curve. Since these curves such as shown in FIGS. 1, 2 and 3 are normal or log-normal with respect to equivalent spherical particle diameter rather than volume, cube root circuits 23, 25 and 27 are incorporated. The Cube root circuits may, for example, be of the type described in U.S. Pat. No. 3,679,884. Cube root circuits 23, 25 and 27 receive the voltages $e_{75}$, $e_{50}$ and $e_{25}$ and, develop voltages at their respective outputs of $e_{75}'$, $e_{50}'$ and $e_{25}'$ which are substantially equal to the cube root of the input voltages. As the equivalent spherical diameter is related to the cube root of the volume, the voltages $e_{75}'$, $e_{50}'$ and $e_{25}'$ are proportional to the equivalent spherical diameter of the corresponding particle sizes.

As we are dealing with a log-normal particulate distribution, the voltages $e_{75}'$, $e_{50}'$ and $e_{25}'$ at the outputs of circuits 23, 25 and 27 are coupled to log calculator circuits 28, 30 and 32 respectively. The log calculators may be of the type described in U.S. Pat. Nos. 3,626,166; 3,237,028; or 3,448,289. The log calculators convert the voltages to their logarithmic equivalent voltages $e_{75}'$, $e_{50}'$ and $e_{25}'$. This is necessary because it is the logarithmic equivalent voltages which are equally spaced with respect to one another as is best shown by FIGS. 1, 2 or 3. The logarithmic equivalent voltage developed at the output of log calculator 28 is coupled via resistor 36 to a junction 38, and the logarithmic equivalent voltage developed at the output of log calculator 32 is coupled via resistor 40 to junction 38. In the preferred embodiment, resistors 36 and 40 are equal to one another.

Resistors 36 and 40 act as a combining network which combines the voltage from log calculator circuit 28 and from log calculator 32 at junction 38 to develop the algebraic average of the voltages at the output of log calculator 28 and log calculator 32 representing the extrapolated approximation or estimate of the 50th percentile based on the 25th and 75th percentiles. This average voltage is coupled from junction 38 of the combining network consisting of resistors 40 and 36 to one input 44 of comparison circuit 46. Comparison circuit 46 is coupled to the output of log calculator 30 and receives the log equivalent output voltage developed at the output of log calculator 30. It should be noted at this point that log calculators 28, 30 and 32 are only necessary if the particulate system is log-normal. If the system is normal the outputs of cube root circuits 23 and 27, are coupled to resistors 36 and 40 respectively and the output of cube root circuit 25 is coupled to input 48 of comparison circuit 46.

Comparison circuit 46 which can for example be a differential amplifier compares the voltages coupled to inputs 44 and 48. If the voltages are equal, indicating that the voltages representing the particle sizes at the 25th, 50th and 75th mass percentiles are correct, comparison circuit 46 will develop a zero or reference level output signal. If the voltages coupled to input 44 and 48 of comparison 46 are unequal, indicating that the previously noted criteria regarding equal spacing, symmetry or linearity have not been met; and that the voltages representing the sizes at the 25th, 50th and 75th mass percentiles are incorrect, comparison circuit 44 will develop an output signal or error signal different from the zero or reference level. The level, or amplitude of the output signal will be functionally related to the difference between the voltages at inputs 44 and 48. The output signal developed by comparison circuit 46, is coupled via conductor 50 and resistor 52 to the input of an integrator amplifier 54. Integrator amplifier 54 develops an output signal in response to the error signal which is coupled to 25th, 50th and 75th percentile circuits 26, 24 and 22 respectively at inputs 56, 58 and 60, respectively. The signal coupled from integrator 54 to inputs 56, 58 and 60 will be combined with the voltages representative of the particle volumes or sizes at the three percentiles modifying these voltages. This feedback process will continue until the voltages developed at the output of circuits 28, 30 and 32, when combined via the summing network consisting of resistors 36 and 40, and compared at inputs 44 and 48 of comparison circuit 46, produces a zero or reference level error signal at the output of comparison signal 46. At that time, the feedback system will have reached an equilibrium state and the voltage representative of the particle sizes for the 25th, 50th and 75th percentiles will have been corrected for inaccuracies due to nondetection of small particles in the particulate system.

Referring again to FIG. 3, curve 64 has been drawn through the sizes representing the 25th, 50th and 75th percentiles of the size distribution of a particulate system being analyzed prior to any corrections for inaccuracies due to nondetection of small particles. As can be seen, the connection of the three points forms a curve rather than a straight line. Because 10% of the particles in the system are too small to be counted, the particle sizes for the 25th, 50th and 75th mass percentiles are larger than is actually the case. Consequently, the points defining curve 64 are incorrect and shifted somewhat to the right as compared to the correct curve 10. Furthermore, because of the nature of operation of the Mass Median apparatus, as hereinafter explained in greater detail, the error introduced for the point representative of a size above which 75% of the particles are distributed will be greater than the error introduced for the size above which 50% of the particles are distributed. This 50% point will have a greater error introduced than the size representative of particles above which 25% of the particles in the system are located.

Figure 5:
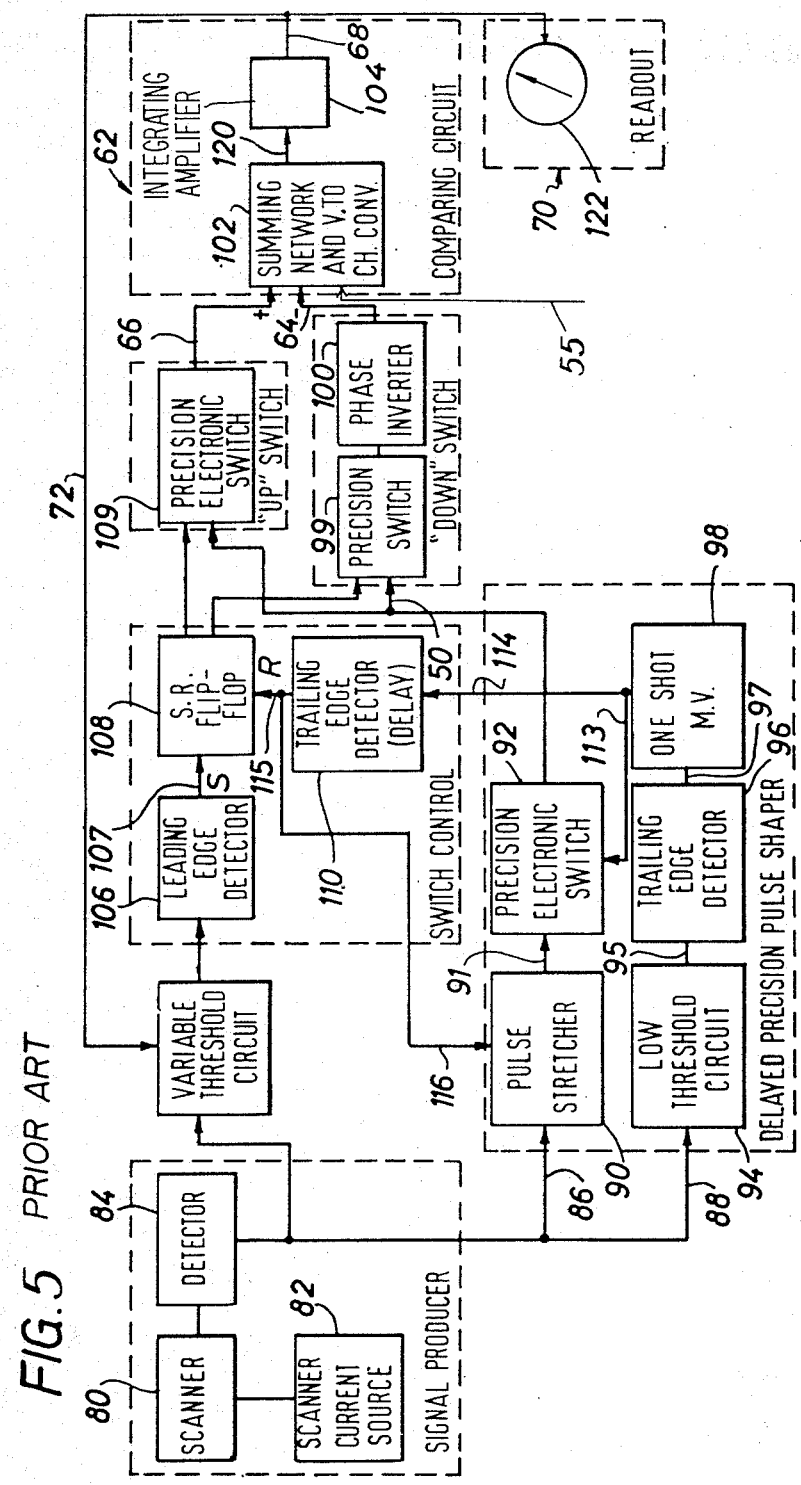
FIG. 5 is a block diagram of a percentile device of FIG. 4.

Referring now to FIG. 5, there is shown a block diagram of the Mass Median apparatus which is identical to that shown in FIG. 6 of the Mass Median patent. Certain numbers for the blocks in this apparatus have been omitted in FIG. 5 in order to prevent confusion between the numbers of those blocks as appearing in the Mass Median patent and the same numbers used in this application. Summing network and voltage to charge convertor 102 in comparison circuit 62 of FIG. 5, is shown as having three inputs. Conductors 66 and 64 are shown as being coupled to two inputs. These two inputs and conductors 64 and 66 are also present in the Mass Median patent. Conductor 55, shown being coupled to the third input of summing network and voltage to charge convertor 102, is the same as conductor 55 shown in FIG. 4. Summing network and voltage to charge convertor 102 may, for example, be a simple summing network consisting of three resistors having first terminals coupled to conductors 64, 66 and 55, respectively, and second terminals coupled together and to output conductor 120. Although a simple resistive summing network is described, it is to be understood that the form of summing network 102 need not be limited to such a structure.

In the Mass Median patent, particle pulses in excess of a particular amplitude, representing particles in excess of a particular size or volume will trip a threshold circuit and cause a positive voltage pulse to be coupled via conductor 66 to summing network and voltage to charge convertor 102. Particle pulses having an amplitude less than this predetermined amplitude will cause a negative voltage pulse to be coupled to summing network and voltage to charge covertor 102 via conductor 64. These positive and negative pulses are converted to charges and coupled to an integrating amplifier 104 for developing an output voltage representative of a particular size particle, which is used to set the threshold previously mentioned. The feedback loop thus created cuased the threshold to seek the level which makes the positive and negative charges equal and therefore the particle size for any particular mass percentile point correct. In the preferred embodiment shown in FIG. 4, the voltage to charge convertors are weighted to yield the output voltage and therefore particle, volume or size for the 75th, 50th and 25th mass percentiles. The voltage developed by integrating amplifier 104 in circuit 26, representing the particle size for the 25th mass percentile will be much less than the voltage developed by amplifier 104 in circuit 22, representing the particle size for the 75th mass percentile. The feedback signal coupled from integrating amplifier 54 via conductor 55 to summing network and voltage to charge convertor 102 in each of the circuits 22, 24 and 26 will be summed in the same manner as the pulse coupled from conductor 64 in order to reduce the voltage representative of the particle size at the 25th, 50th and 75th mass percentile. Furthermore, the feedback signal will have a greater effect upon the voltage representing the particle size at the 25th mass percentile at the output of circuit 26 than it will upon the output voltage representing the particle size at the 75th percentile at the output of circuit 22 because it will be a greater percentage of one than of the other. Referencing this is curve 64 in FIG. 3, it can be seen that although an equal error or correction voltage is coupled to all three circuits 22, 24 and 26, it will modify the sizes in a nonlinear fashion so as to correct for the nonlinearity in curve 64 and cause the three points shown thereon to linearly align as represented by curve 10.

The above described apparatus extrapolates by combining the two outer points to estimate the center point. Other extrapolation systems may be employed if the system meets the criterias noted above. For example the upper and middle points could be combined then reduced by a known percentage to approximate the lower point. The approximated point could then be compared to the measured signal to obtain an error signal.

It is to be understood that the method heretofore described, for ascertaining whether the criteria of symmetry, equal spacing, or linearity, have been met, by a comparison of three particle sizes, or voltages representative of the particle sizes, acertained by the passage of the particulate system through three Mass Median apparatuses is also to be consicered as within the scope of the invention. Additionally, it should be understood that the invention is capable of being embodied in structures which differ in detail considerably from those described, but without departing from the spirit or scope of the invention as defined in the appended claims.

What it is desired to secure by Letters Patent of the United States is:

1. A method for ascertaining a plurality of correct particle sizes within a particulate system below which sizes predetermined fractions of the total mass of the system are respectively included, and wherein the particulate system is passed through a particle detecting device which produces particle pulses proportional to the size of the particles passed therethrough, said method including in combination, developing first, second and third particle size signals in response to said particle pulses indicative respectively of first, second and third particle sizes below which sizes first, second and third predetermined fractions respectively of the total mass of the system are included, combining said first and second particle size signals to develope a combined signal, comparing said combined signal and said third particle size signal and developing a comparison signal which varies in accordance with the difference therebetween, varying said first, second and third particle size signals in accordance with said comparison signal for correcting said first, second and third particle size signals.

2. The method of claim 1 wherein said step of combining said first and second particle size signals includes the step of algebraically averaging said first and second particle size signals.

3. The method of claim 1 wherein said step of developing said first, second and third particle size signals includes the step of developing first, second and third particle size signals indicative of first, second and third particle sizes below which sizes one-quarter, three-quarters and one-half respectively of the total mass of the system is included.

4. The method of claim 1 wherein said step of varying said first, second and third particle size signals includes the step of decreasing said first, second and third signals by a predetermined amount in accordance with the comparison signal.

5. The method for determining the correct particle sizes at predetermined percentiles of the size distribution of a particulate system wherein the particulate system is passed through a particle detecting device which produces particle pulses proportional to the particle sizes, said method including the steps of,
developing first, second and third particle size signals, in response to said particle pulses, indicative of the size of the particules in the particulate system at first, second and third percentiles respectively,
comparing said first, second and third particle size signals to one another for ascertaining whether said particle size signals have a specific relationship to one another,
varying said first, second and third particle size signals in accordance with the variation from said specific relationship for ascertaining the correct particle sizes at said predetermined percentiles of the size distribution of the particulate system.

6. The method of claim 5 further including the steps of:
developing a comparison signal which varies in accordance with the variation from said specific relationship of said first, second and third particle size signals with respect to one another,
and wherein said varying of said first, second and third particle size signals includes varying said first, second and third signals in accordance with said comparison signal for ascertaining the correct particle sizes at said predetermined percentiles of the size distribution of the particulate system.

7. The method of claim 5 wherein said step of comparing said first, second and third particle size signals to one another for ascertaining whether said particle size signals have a specific relationship to one another includes the step of comparing said first, second and third particle size signals to one another to ascertain whether one of the specific relationships of linearity, symmetry and equal spacing of each of said particle size signals exist with respect to one another.

8. An apparatus for ascertaining a plurality of correct particle sizes within a particulate system below which sizes predetermined fractions of the total mass of the system are respectively included, and wherein the particulate system is passed through a particle detecting device which produces particle pulses proportional to the size of the particles passed therethrough, said apparatus including in combination,
at least first, second and third particle size determing circuits having a common input coupled to the particle detecting device and operative in response to the particle pulses to develop first, second and third particle size signals respectively indicative of first, second and third particle sizes below which sizes first, second and third predetermined fractions of the total mass of the system are included,
combining means coupled to said first and second particle size determining circuits for combining said first and second particle size signals and developing a combined signal therefrom,
comparison means coupled to said combining means and said third particle size determining circuit and operative to compare said combined signal and said third particle size signal and develop a comparison signal which varies in accordance with the differences therebetween, said first, second and third particle size determining circuits being coupled to said comparison means and operative in response to said comparison signal to vary said first, second and third particle size signals.

9. The apparatus of claim 8 wherein said combined signal is the average of said first and second particle size signals.

10. The apparatus of claim 8 wherein said comparison means is a comparator.

11. The apparatus of claim 8 wherein said combining means includes, first impedance means having a first terminal coupled to said first particle size determining circuit, and a second terminal coupled to said comparison means, and second impedance means having a first terminal coupled to said second particle size determining circuit, and a second terminal coupled to first impedance means second terminal.

12. The apparatus of claim 11 wherein the impedance of said first and second impedance means are selected such that the combined signal is substantially equal to the third particle size signal when the first, second and third particle size signals are correct.

13. The apparatus of claim 8 wherein said first and second predetermined fractions of the total mass of the system are respectively above and below said third predetermined fraction of the total mass of the system, and are substantially equally spaced therefrom.

14. The apparatus of claim 8 wherein said first, second and third predetermined fractions of the total mass of the system are three-quarters, one-quarter, and one-half respectively.

15. The apparatus of claim 8 wherein said particulate system has a log-normal distribution of particle sizes therein, and said first, second and third particle size signals represent the logarithm of said first, second and third particle sizes.

16. The apparatus of claim 8 wherein said first, second and third particle size determining circuits each include a determining circuit combining means for combining electrical quantities indicative of the particles in said system above and below the particle size and for developing said particle size signal, said determining circuit combining means being coupled to said comparison means and operative in response to said comparison signal to vary said electrical quantity below the particle size.

17. An apparatus for determining the correct particle sizes at particular percentiles of the size distribution of a particulate system, wherein the particulate system is passed through a particle detecting device which produces particle pulses proportional to the particle sizes including in combination,
first, second and third percentile size determining circuits coupled to said particle detecting device and operative in respoinse to said particle signals to develop first, second and third particle size signals respectively indicating the size of the particles in the particulate system at first, second and third percentiles, said first, second and third particle size signals having a predetermined relationship with respect to one another,
combining means coupled to said first and second percentile size determining circuits for combining said first and second particle size signals and developing a combined signal therefrom, comparison means having an output, and an input coupled to said combining means and to said third percentile size determining circuit, said comparison means being operative to compare said combined signal and said third particle size signal and develop an error signal in accordance with the difference therebetween, said first, second and third percentile size determining circuits being coupled to said comparison means and operative in response to said error signal to vary said first, second and third particle size signals.

18. The apparatus of claim 17 wherein said combined signal is the average of said first and second signals.

19. The apparatus of claim 17 wherein said first and second percentiles are equally removed from said third percentile.

20. The apparatus of claim 19 wherein said first percentile point is below said third percentile point and said second percentile point is above said third percentile point.

21. The apparatus of claim 17 wherein said comparison means is a differential amplifier.

22. The apparatus of claim 17 wherein said first, second and third particle size signals and percentiles have a specific relationship with respect to one another.

23. The apparatus of claim 22 wherein said specific relationship is one of linearity, symmetry and equal spacing of said particle size signals and percentiles with respect to one another.

24. An apparatus for determining the correct particle sizes at predetermined percentiles of the size distribution of a particulate system wherein the particulate system is passed through a particle detecting device which produces particle pulses proportional to the particle sizes including in combination, first, second and third percentile size determining circuits coupled to said particle detecting device and operative in response to said particle pulses to develop first, second and third particle size signals respectively, indicating the size of the particles in the particulate system at first, second and third percentiles, said first, second and third particle size signals at said first, second and third percentiles having a predetermined relationship with respect to one another, comparison means coupled to said first, second and third percentile size determining circuits and operative to compare said first, second and third particle size signals for determining the existence of said predetermined relationship, said comparison means being operative to develop a comparison signal in accordance with variations from said predetermined relationship, said first, second and third percentile size determining circuits being further coupled to said comparison means and operative in response to said comparison signal to vary said first, second and third particle size signals for achieving said predetermined relationship therebetween.

25. The apparatus of claim 24 wherein said predetermined relationship is one of linearity, symmetry and equal spacing of said first, second and third particle size signals at said first, second and third percentiles.

26. The apparatus of claim 24 wherein said first percentile point is below said third percentile and said second percentile is above said third percentile, said first and second percentiles being equally spaced from said third percentile.

* * * * *

UNITED STATES PATENT OFFICE
CERTIFICATE OF CORRECTION

Patent No. 3,944,797     Dated March 16, 1976

Inventor(s) Wallace H. Coulter et al.     Pate 1 of 2

It is certified that error appears in the above-identified patent and that said Letters Patent are hereby corrected as shown below:

Column 1,     line 61, change "particules" to -- particles --.

Column 5, line 31, change "50the" to -- 50th --.

Column 7, line 45, change "cuased" to -- causes --;

line 68, after "75th" insert -- mass --.

Column 8, line 2, change "is" to -- to --;

line 24, change "consicered" to -- considered --;

line 49, change "develope" to -- develop --;

line 66, after "sizes" insert -- respectively --.

UNITED STATES PATENT AND TRADEMARK OFFICE
CERTIFICATE OF CORRECTION

PATENT NO. : 3,944,797
DATED : March 16, 1976
INVENTOR(S) : Wallace H. Coulter et al It is certified that error appears in the above–identified patent and that said Letters Patent are hereby corrected as shown below:

Column 9, line 14, change "particules" to -- particles --;

Signed and Sealed this

Fifth Day of April 1977

[SEAL]

Attest:

RUTH C. MASON
*Attesting Officer*

C. MARSHALL DANN
*Commissioner of Patents and Trademarks*